US006652494B1

(12) United States Patent
Dragan et al.

(10) Patent No.: US 6,652,494 B1
(45) Date of Patent: Nov. 25, 2003

(54) UNIT DOSE LOW VISCOSITY MATERIAL DISPENSING SYSTEM WITH EASY LOADING

(75) Inventors: William B. Dragan, Easton, CT (US); Gordon Rowe, Wallingford, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 09/853,419

(22) Filed: May 11, 2001

Related U.S. Application Data

(63) Continuation-in-part of application No. 09/399,891, filed on Sep. 21, 1999, now Pat. No. 6,328,715.

(51) Int. Cl.[7] .................. A61M 5/00; A61M 5/178; G01F 11/06; B65D 88/54
(52) U.S. Cl. .................. 604/235; 604/212; 222/327
(58) Field of Search .................. 604/235, 212, 604/200, 187, 93.01, 61, 38, 37, 36, 220; 222/137, 327, 325

(56) References Cited

U.S. PATENT DOCUMENTS

| | | |
|---|---|---|
| 2,994,323 A | 8/1961 | Dann et al. |
| 3,780,735 A * | 12/1973 | Crouter et al. ............ 604/218 |
| 3,884,231 A | 5/1975 | Peters |
| 3,900,954 A | 8/1975 | Dragan |
| 3,955,719 A | 5/1976 | Pheuipin |
| 4,392,491 A | 7/1983 | Takasugi et al. |
| 4,795,444 A | 1/1989 | Hasegawa et al. |
| 4,972,969 A | 11/1990 | Randklev |
| 5,125,836 A | 6/1992 | Dragan et al. |
| 5,129,825 A | 7/1992 | Discko, Jr. |
| 5,320,257 A | 6/1994 | Snedden |
| 5,346,481 A | 9/1994 | Bunin |
| 5,489,207 A | 2/1996 | Dragan et al. |
| 5,496,286 A * | 3/1996 | Stiehl et al. .............. 604/232 |
| 5,827,233 A | 10/1998 | Futagawa et al. |
| 6,328,715 B1 * | 12/2001 | Dragan et al. ............ 604/232 |

FOREIGN PATENT DOCUMENTS

| | | |
|---|---|---|
| DE | 217162 | 4/1908 |
| DE | 7837177 | 3/1979 |
| DE | 33 44 345 A1 | 6/1985 |
| DE | 44 19 235 A1 | 12/1995 |
| DK | 32825 | 1/1924 |
| EP | 0 919 206 A2 | 6/1999 |
| EP | 1 086 661 A2 | 3/2001 |
| GB | 787090 | 12/1957 |

* cited by examiner

*Primary Examiner*—Brian L. Casler
*Assistant Examiner*—Mark K. Han
(74) *Attorney, Agent, or Firm*—Fattibene & Fattibene; Arthur T. Fattibene; Paul A. Fattibene

(57) ABSTRACT

A syringe having a breech and a slot adjacent an ampule chamber adapted to receive the body and nozzle of a collapsible ampule. A syringe includes a forward ampule chamber having a predetermined longitudinal length for dispensing a relatively low viscosity material. A closed ampule containing a relatively low viscous material is collapsible and is easily positioned and held within the syringe during dispensing. The nozzle slot permits easy insertion of the flexible collapsible ampule and removal once the ampule is collapsed. In one embodiment, a syringe barrel has flexible fingers used in combination with a plunger having a reduced diameter intermediate portion for preventing the plunger from falling out of the barrel. Low viscosity materials in a unit dose collapsible ampule are controllably and conveniently dispensed for use in many different applications. The present invention is particularly suitable for dispensing dental materials.

10 Claims, 4 Drawing Sheets

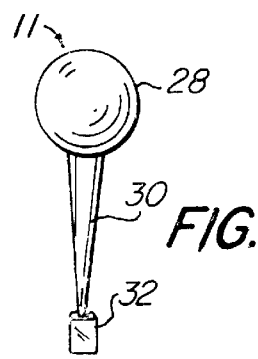
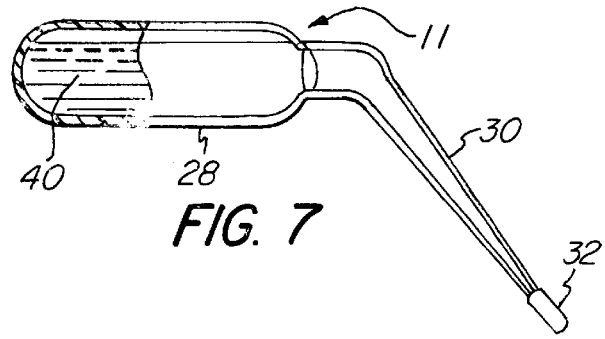
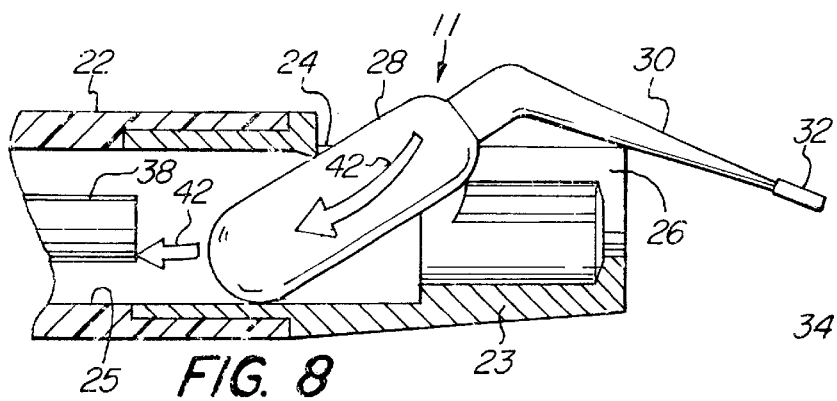
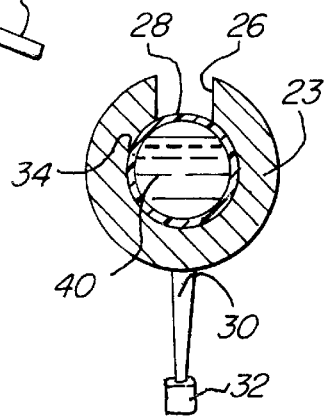
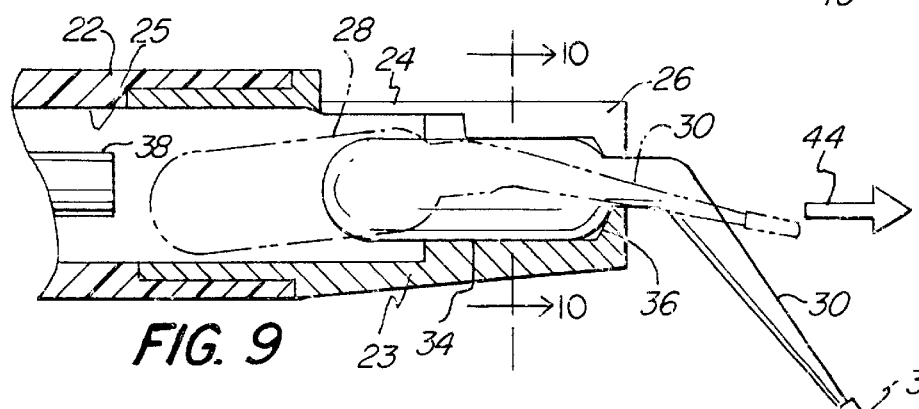
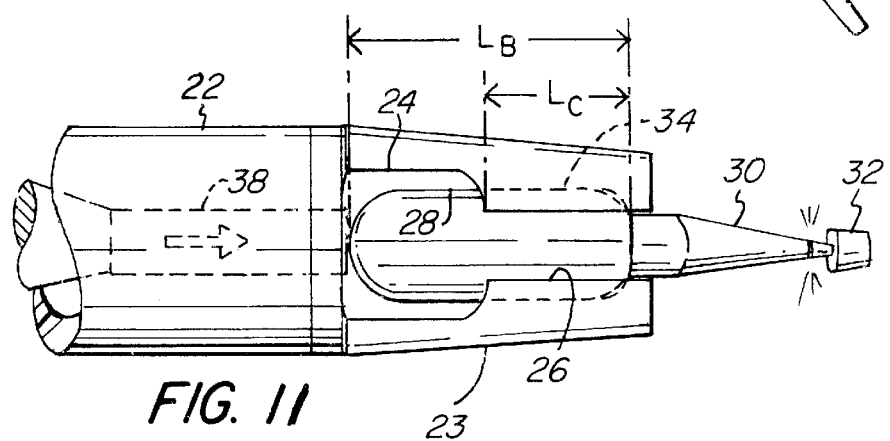

UNIT DOSE LOW VISCOSITY MATERIAL DISPENSING SYSTEM WITH EASY LOADING

RELATED APPLICATION

This application is a continuation-in-part of U.S. patent application Ser. No. 09/399,891 filed Sep. 21, 1999, now U.S. Pat. No. 6,328,715.

FIELD OF THE INVENTION

The present invention relates in general to the placement of low viscosity material, and particularly to a collapsible ampule that is easily loaded into a syringe for dispensing the low viscosity material.

BACKGROUND OF THE INVENTION

In many applications such as medical and industrial applications, and in particular dentistry, it is often desirable to dispense and accurately place a low viscosity material. Many devices have been developed, in particular within dentistry, to apply a high viscosity material such as composite filling material used to restore teeth. In these applications, cartridges containing relatively viscous material are dispensed with a syringe having a mechanical advantage. One such syringe is disclosed in U.S. Pat. No. 5,125,836 entitled "Easy Loading Material Cartridge For Viscous Material" issuing to Dragan et al on Jun. 30, 1992. Therein disclosed is a syringe having a mechanical advantage used in dispensing viscous material from a cartridge. While this device discloses an apparatus for dispensing of relatively high viscosity materials, which are difficult to extrude, there is often a need to dispense low viscosity materials such as fluids and gels, in a controlled manner and dose.

Generally, low viscosity materials are applied on a surface or in a cavity. Often, dispensing of these relatively low viscosity materials, including fluids and gels, is done by brushing or dabbing with a handheld applicator. One technique for dispensing relatively small volumes of low viscosity material is by placing a quantity of the low viscosity material into a dropper type device, such as an ampule, which may be filled with the liquid or gel to be dispensed. One such device is disclosed in U.S. Pat. No. 5,320,257 entitled "Resilient Ampule With Articulating Linkage And Elongated Spout" issuing to Snedden on Jun. 14, 1994. Therein disclosed is an elongated ampule having a reservoir bulb on one end and an elongated spout on the other end with an articulating linkage or bellows therebetween.

Another device for dispensing a liquid medicament is disclosed in U.S. Pat. No. 5,827,233 entitled "Pre-filled Syringe" and issuing to Futikawa et al on Oct. 27, 1998. Therein disclosed is a pre-filled syringe having a flexible hollow cylinder body containing a liquid medicament inserted into the barrel.

While many of these prior devices have adequately dispensed material, they have often been difficult to use or have resulted in difficulty in removing an expended cartridge or ampule from the barrel of the syringe. Therefore, there is a need for an improved and more convenient apparatus and method for dispensing low viscosity materials easily and in a controlled manner with a single dose system.

SUMMARY OF THE INVENTION

The present invention relates to a delivery system using collapsible ampules that is easy to load and easy to remove the collapsed ampule after dispensing of a relatively low viscosity material, such as a liquid or a gel. The invention comprises a syringe having a barrel with a breech opening therein. Forward of the breech opening is a slot having a longitudinal length. The barrel is undercut forward of the breech opening under the slot to receive a substantial length of a body portion of the collapsible ampule and forms an ampule chamber. The undercut portion receives at least one half of the longitudinal length of the body portion of the collapsible ampule. The slot is sized to easily receive a nozzle portion of the collapsible ampule. Accordingly, a substantial portion of the body of the collapsible ampule securely fits within the undercut portion of the barrel and rests adjacent a forward end wall with a nozzle portion of the collapsible ampule extending there through. A rear portion of the collapsible ampule body extends into the breech opening in the barrel. In one embodiment of the syringe, a levered handle portion is utilized to aid in controlled dispensing of the material contained within the collapsible ampule. In another embodiment of the present invention, a tubular barrel is utilized having a plunger slidably moving therein. In another embodiment of the present invention, flexible fingers are used at the rear opening of the barrel of the syringe and a plunger having an intermediate reduced diameter portion is placed within the barrel. The flexible fingers retain the plunger within the barrel portion and prevent the plunger from falling out of the barrel of the syringe.

Accordingly, it is an object of the present invention to provide a syringe for dispensing a relatively low viscosity fluid or gel contained within a collapsible ampule.

It is an advantage of the present invention that control of the dispensing of low viscosity fluids is improved.

It is another advantage of the present invention that low viscosity fluids may be dispensed in a measured amount.

It is a feature of the present invention that an ampule chamber holds more than one-half of a body portion of a collapsible ampule.

It is another feature of the present invention that a slot is adapted to receive an pass through the nozzle of a collapsible ampule.

It is yet another feature of the present invention that flexible fingers extend into the bore of the barrel preventing a plunger having a reduced intermediate diameter from falling out of the barrel.

These and other objects, advantages, and features will become readily apparent in view of the following more detailed description.

BRIEF DESCRIPTION OF THE DRAWINGS

FIG. 6 is the rear end view of a collapsible ampule.

FIG. 7 is a side elevational view of a collapsible ampule in partial cross section.

FIG. 8 is a cross section of a front portion of a barrel illustrating insertion of a collapsible ampule.

FIG. 9 is a cross section of a front portion of a barrel illustrating the positioning of a collapsible ampule therein.

FIG. 10 is a cross section taken along line 10—10 in FIG. 9.

FIG. 11 is a top-plan view of a portion of a barrel illustrating the collapsible ampule placed therein.

DETAILED DESCRIPTION OF THE PREFERRED EMBODIMENTS

Figure 1:
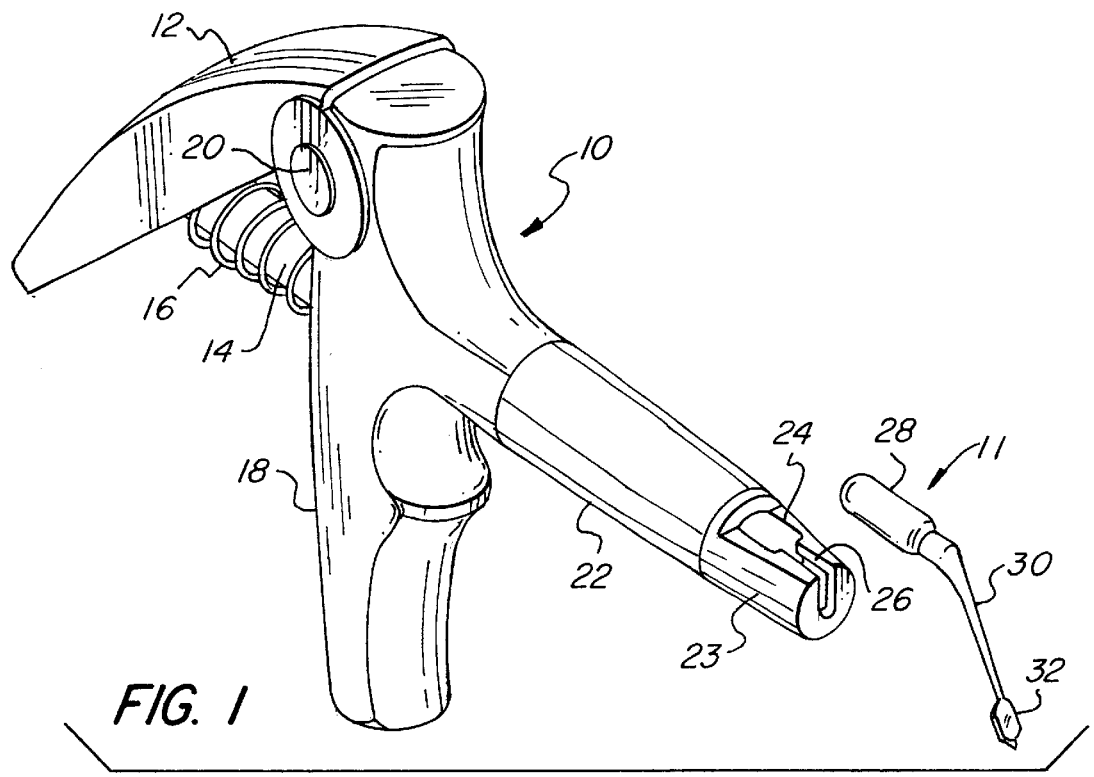
FIG. 1 is a perspective view of an embodiment of the present invention.

FIG. 1 is a perspective view illustrating an embodiment of the present invention having a lever to assist dispensing of a material. The syringe 10 comprises a rear handle 12 pivotally attached to a front handle 18 by a pin 20. Attached to the front handle 18 is a barrel 22. A plunger 14 is slidably placed within the handle 18 and extends into the barrel 22. A spring 16 biases the plunger 14 away from the barrel 22. The end of the plunger 14 contacts the inner surface of rear handle 12 forming a camming action when rear handle 12 is moved closer to front handle 18. This advances the plunger 14 forward into the barrel 22. Barrel 22 has an insert 23 which may be metal. Alternatively, the barrel 22 and insert 23 may be molded from a single piece of material. Insert 23 has a breech opening 24 to receive the body 28 of a collapsible ampule 11. Between the distal end of the insert 23 and the breech opening 24 is a longitudinal slot 26. The longitudinal slot 26 has a lateral dimension sized or adapted to receive the nozzle 30 of the collapsible ampule 11. The collapsible ampule 11 contains a low viscosity material, such as a liquid or a gel for dispensing. The nozzle 30 of the collapsible ampule 11 is sealed with a seal 32. Therefore, the entire collapsible ampule is initially sealed and provides a single or unit dose of material to be dispensed.

Figure 2:
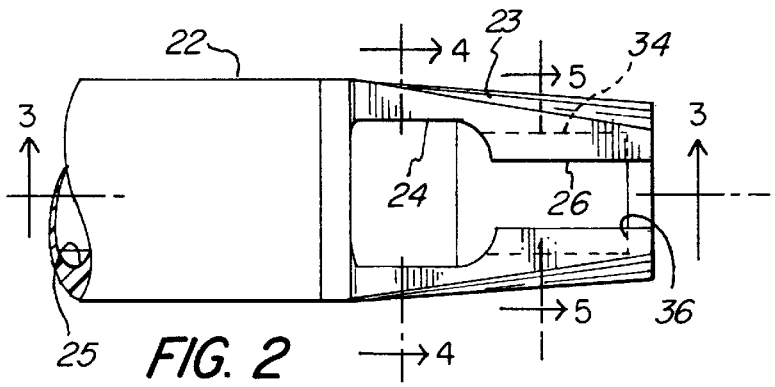
FIG. 2 is a plan view of the front portion of the barrel illustrated in FIG. 1.

FIG. 2 more clearly illustrates the forward portion of barrel 22 and the insert 23. Within the insert 23 and forward of the breech opening 24 is formed an ampule chamber 34. Ampule chamber 34 has a lateral dimension or diameter that approximates the body 28 of ampule 11, illustrated in FIG. 1. However, in view of the relatively easy access to the collapsible ampule 11 and nozzle 30, the ampule 11, illustrated in FIG. 1, once collapsed, is easily removed from the syringe. Additionally, because the ampule chamber 34 substantially retains the ampule 11, and the ampule 11 is collapsible or not rigid, a range of different size ampules may be easily accommodated with a single syringe. That is, the diameter of the ampule chamber 34 may be slightly larger or smaller than the diameter of the collapsible ampule 11. The ampule 11 conforms to the shape of the ampule chamber 34 and slot 26 yet is easily removable after use.

Figure 3:
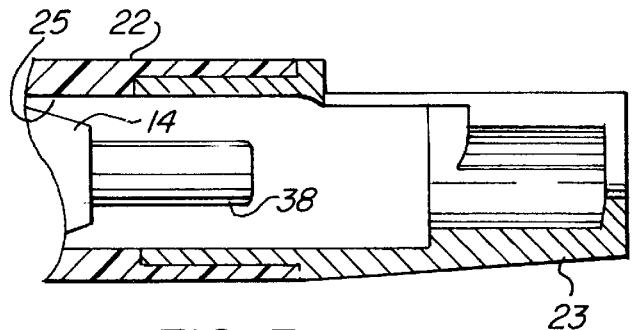
FIG. 3 is a cross section taken along line 3—3 in FIG. 2.

FIG. 3 is a cross section taken along line 3—3 in FIG. 2. The plunger 14 is illustrated having a plunger front 38 of a constant diameter. The relatively easy access to the ampule in the present invention prevents the need for a plunger having a modified design to extract the expended and collapsed ampule. However, to facilitate removal of the ampule, the plunger front 38 may be modified to have a mushroom shaped end such as that illustrated in related U.S. patent application ser. No. 09/399,891 filed Sep. 21, 1999 entitled "Unit Dose Low Viscosity Material Dispensing System", which is herein incorporated by reference. Therein disclosed is a number of plunger front ends having different configurations to facilitate easy removal of an used, expended or collapsed ampule.

Figure 4:
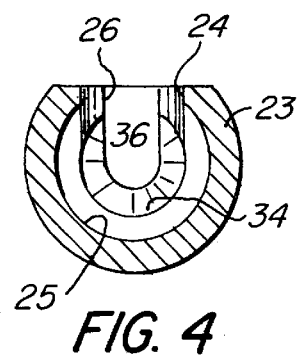
FIG. 4 is a cross section taken along line 4—4 in FIG. 2.

FIG. 4 is a cross section taken along line 4—4 in FIG. 2. FIG. 4 more clearly illustrates the different lateral dimensions or diameters within the insert 23. Insert 23 has bore 25 and ampule chamber 34. At the forward end of the ampule chamber 34 is shoulder 36. Breech opening 24 is formed within the insert 23, as is the slot 26. It should be noted that slot 26 is a relatively small, lateral dimension opening and that a substantial portion of the walls of the insert 23 form part of the ampule chamber 34. By substantial portion it is meant that the walls extend more than one hundred and eighty degrees around the collapsible ampule body 28. Accordingly, the ampule chamber provides substantial support for the body 28 of the collapsible ampule 11, illustrated in FIG. 1.

Figure 5:
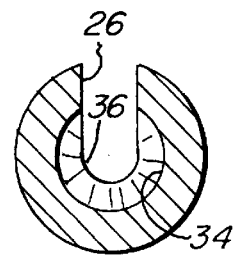
FIG. 5 is a cross section taken along line 5—5 in FIG. 2.

FIG. 5 is a cross section taken along line 5—5 illustrated in FIG. 2 and better illustrates the shoulder 36 formed adjacent the distal end of the insert 23. The shoulder 36 may be formed as a portion of a hemisphere to more securely receive the curved end of the body portion 28 of the ampule 11, illustrated in FIG. 1.

FIGS. 6–7 illustrate a collapsible ampule 11. FIG. 7 is a partial cross-section of the collapsible ampule 11 illustrating material 40 therein. The material is typically a relatively low viscosity liquid or gel. The material preferably is a dental material for placement in an oral cavity. The body portion 28 of the collapsible ampule 11 is made of a relatively thin, flexible plastic material that can easily collapse or have an end portion forced inward towards the nozzle 30 to dispense the material. Before dispensing, the seal on nozzle 30 is removed by cutting, breaking, tearing or snapping off.

FIG. 8 is a cross section illustrating the ease in which the collapsible ampule 11 is placed within the breech opening 24 in insert 23. The nozzle 30 easily passes through the slot 26 adjacent the distal end of the insert 23.

FIG. 9 illustrates the ampule 11 moved forward into position within the ampule chamber 34. The nozzle 30 is pulled in the direction of arrow 44 through an opening in the distal end adjacent the shoulder 36. A rear portion of the collapsible ampule 11 extends under the breach opening 24.

FIG. 10 is a cross section taken along line 10—10 in FIG. 9. The insert 23 having the chamber 34 therein holds the body portion 28 of the collapsible ampule securely. The insert portion 23 extends a substantial portion around the body 28. Accordingly, the diameter of the body 28 may vary slightly with the diameter of the ampule chamber 34 and yet the collapsible body 28 will still be securely contained within the ampule chamber 34. Additionally, because of the slot 26 and the breech 24, illustrated in FIGS. 8 and 9, the collapsed capsule 11 can be easily removed from the insert 23. Removal of a collapsible capsule has often been a problem in prior dispensers.

FIG. 11 is a plan view more clearly illustrating the relationship between the body 28 of the collapsible ampule, the breech 24 and the longitudinal length of the ampule chamber 34. A substantial portion of the ampule chamber 34 is formed under the slot 26. The longitudinal length of the ampule chamber 34 is illustrated as $L_C$. The longitudinal length of the body 28 of the collapsible ampule is illustrated as $L_B$. It should be appreciated that a substantial portion of the longitudinal length of the body 28 of the ampule is retained within the ampule chamber 34. The longitudinal length $L_C$ of the ampule chamber 34 may be at least or greater than one-half of the longitudinal length $L_B$ of the ampule body. Preferably, the longitudinal length $L_C$ of the ampule chamber 34 is between three-quarters or seventy five percent and nine tenths or ninety percent of the longitudinal length $L_B$ of the ampule body 28. Accordingly, preferably at least three-quarters of the longitudinal length $L_B$ of the ampule body 28 is securely retained within the ampule chamber 34. However, depending upon the flexibility or rigidity of the ampule, more or less of the ampule body 28 may be contained within the ampule chamber 34. The ampule chamber 34 must contain a sufficient portion of the ampule to prevent the rear of the ampule from being displaced laterally when contacted by the plunger front 38.

Figure 12:
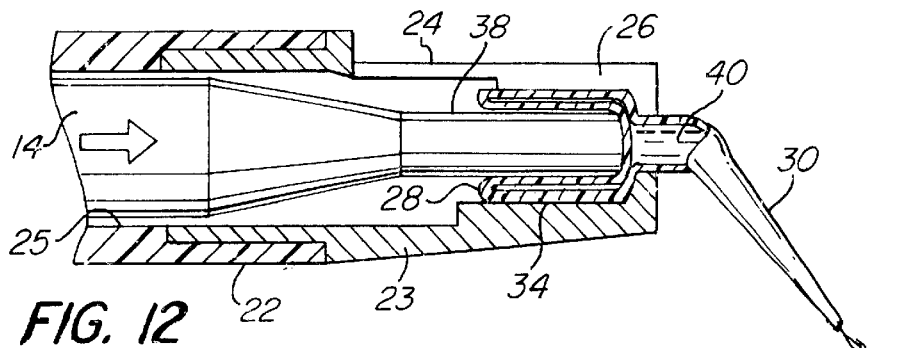
FIG. 12 is a cross section of a portion of a barrel illustrating an expended or dispensed collapsed ampule.

FIG. 12 is a partial cross section illustrating the body 28 of the ampule folded over onto itself for dispensing the material 40 contained therein. The plunger front 38 forces a rear portion of the body 28 forward causing the collapsible ampule to collapse. Once the plunger 14 is withdrawn from the ampule chamber 34, the collapsed ampule may easily be removed from the insert 23 by pushing on nozzle 30 forcing the collapsed body 28 into the larger bore 25 of the barrel 22 so that the collapsed ampule can easily be removed from the breech 24 and the nozzle 30 can be removed through slot 26. Accordingly, it is nearly impossible for the collapsed ampule to be jammed or become irremovable from the syringe.

Figure 13:
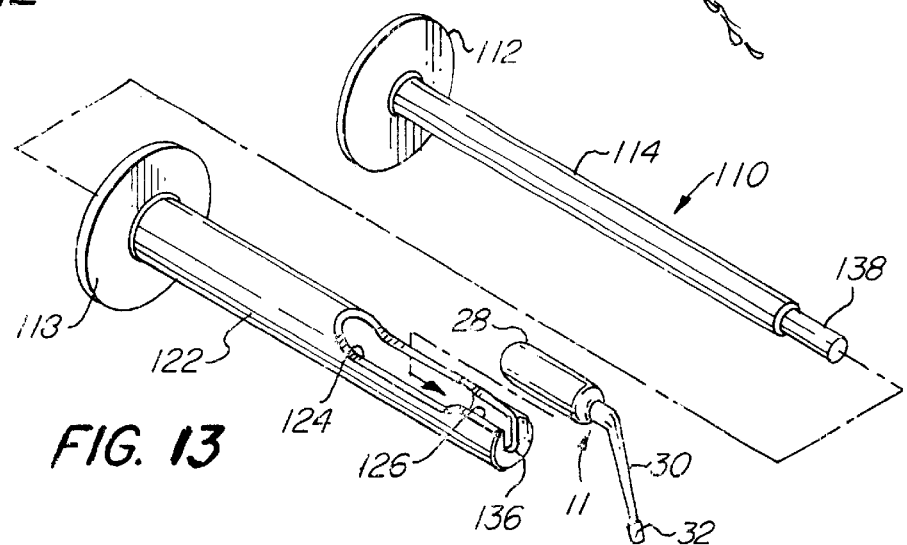
FIG. 13 is a perspective view of another embodiment of the present invention.

FIG. 13 illustrates another embodiment of the present invention utilizing a syringe without a lever. The syringe 110 comprises a plunger 114 having a handle 112 and a plunger front 138. A barrel 122 has a diameter sized to receive the plunger 114. The barrel 122 has a front handle 118 on one end. On the other end is a side opening or breech 124 adjacent the slot 126. The body portion 28 of collapsible ampule 11 is placed through the breech 124 with the nozzle 30 passing through slot 126. The collapsible capsule 11 is then pulled forward by grasping nozzle 30 such that the collapsible body portion 28 is forced against shoulder 136. A substantial portion of a front end of the barrel 122 securely retains the body 28 of the collapsible ampule 11.

Figure 14:
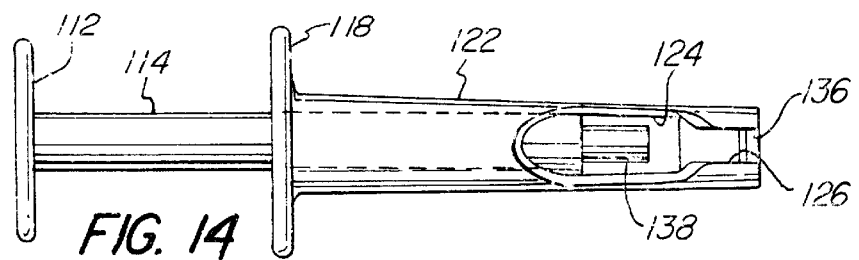
FIG. 14 is a plan view of the embodiment illustrated in FIG. 13.

FIG. 14 more clearly illustrates the different lateral dimension of the breech 124 and the slot 126.

Figure 15:
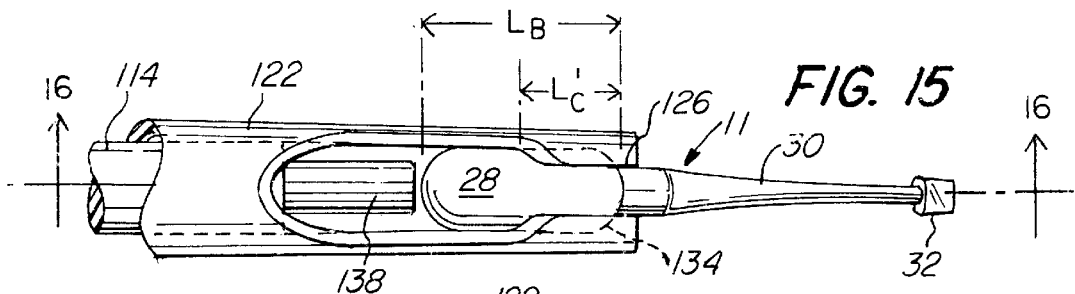
FIG. 15 is a plan view of a portion of the barrel having a collapsible ampule placed therein.

FIG. 15 more clearly illustrates the secure retaining of the collapsible ampule 11 within the barrel 122 of the syringe. The body 28 of the collapsible ampule 11 has a longitudinal length $L_B$. An ampule chamber 134 formed by the sidewalls of the barrel 122 encompasses a substantial portion of the collapsible body 28 and has a longitudinal length $L'_C$. The longitudinal length $L'_C$ of the ampule chamber 134 is greater than one-half of the longitudinal length of the body 28, and is preferably three-quarters or more of the longitudinal length LB. Accordingly, by retaining a substantial portion of the collapsible body 28 and providing a slot 126 through which the nozzle 30 may pass makes removal of the collapsible ampule 11, once expended, relatively easy. The relatively easy placement and removal of the ampule 11 is achieved, irrespective of the angle in which nozzle 30 is with respect to the body 28. A relatively large angle between the longitudinal axis of the body 28 and the longitudinal axis of the nozzle 30 often resulted in difficulty in placing an ampule and removing the expended ampule from prior syringes.

Figure 16:
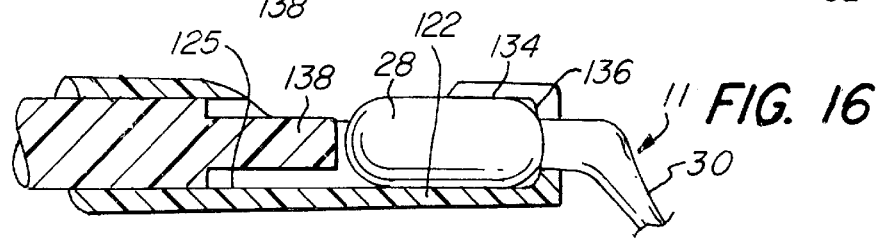
FIG. 16 is a cross section taken along line 16—16 in FIG. 15.

FIG. 16 is a cross section taken along line 16—16 in FIG. 15 and illustrates the placement of the ampule 11 within the ampule chamber 134.

Figure 17:
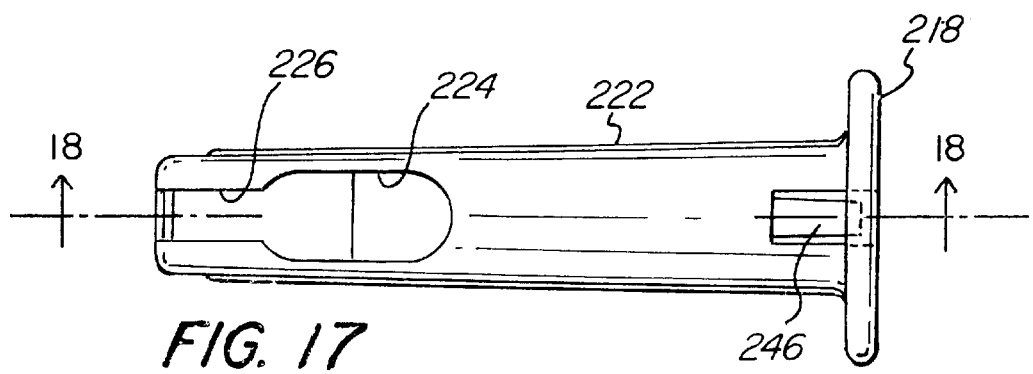
FIG. 17 is a plan view of the barrel of another embodiment of the present invention.

FIGS. 17–20 illustrate another embodiment of the present invention. This embodiment illustrates a means for retaining a plunger within the barrel as well as a means for stopping the advancement of the plunger. FIG. 17 is a plan view illustrating the barrel 222 of a syringe. The barrel 222 has a side opening or breech 224 and a slot 226 extending from the breech 224 to the distal end. Adjacent a front handle 218 and the rear opening are flexible fingers 246.

Figure 18:
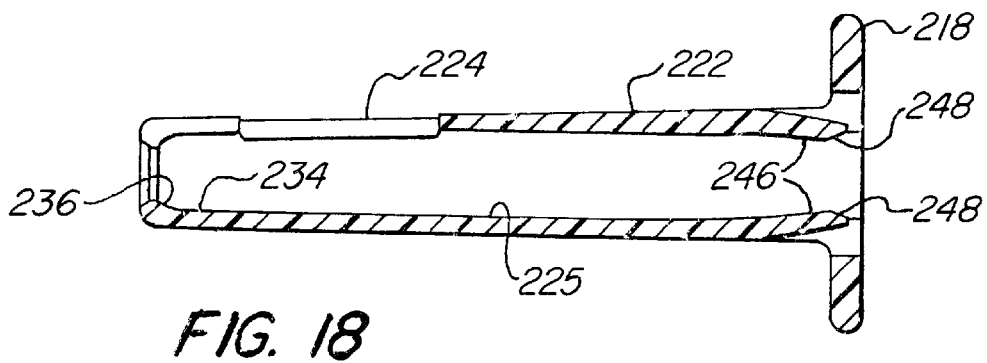
FIG. 18 is a cross section taken along line 18—18 in FIG. 17.

FIG. 18 is a cross section taken along line 18—18 in FIG. 17. FIG. 18 more clearly illustrates the shoulder 236 adjacent the end through which the nozzle of the collapsible ampule extends and the ampule chamber 234 in which the collapsible ampule is placed. In this embodiment, the bore 225 of the syringe 222 is substantially uniform. However, fingers 246 extend radially into the bore 225 of the syringe 222. Beveled or angled surfaces 248 are formed on one end of the flexible fingers 246. Preferably, the flexible fingers 246 are molded directly or integrally into the barrel 222 of the syringe. Preferably, the syringe is a single molded piece made of a suitable plastic.

Figure 19:
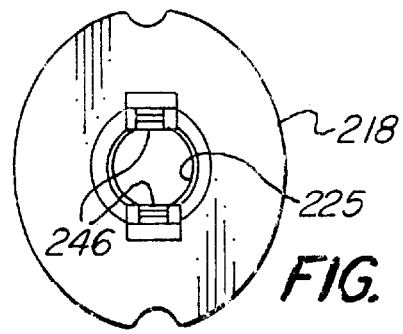
FIG. 19 is an end elevational view of the embodiment of the present invention illustrated in FIG. 18.

FIG. 19 illustrates the rear open end adjacent the front handle 18 of the syringe barrel. Flexible fingers 246 project radially into the bore 225. Accordingly, the distance between the fingers 246 is less than the diameter of the bore 225.

Figure 20:
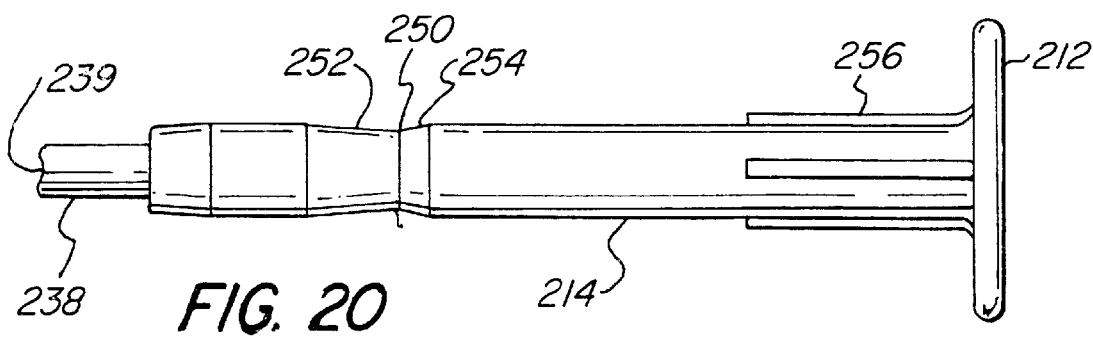
FIG. 20 is a side elevational view of a plunger utilized with the barrel in the embodiment illustrated in FIGS. 17–19.

FIG. 20 illustrates a plunger 214 for use in bore 225 of the syringe body illustrated in FIGS. 17–19. The plunger 214 has a rear handle 212 and a plunger front 238. The plunger front 238 may have a concave front surface 239. The concave front surface 239 may match the hemispherical end of a collapsible ampule. This helps to prevent lateral movement of the ampule body during dispensing. Intermediate the longitudinal length of the plunger 214 is a reduced diameter 250. On either side of the reduced intermediate diameter 250 is a front ramp 252 and a rear ramp 254. The reduced intermediate diameter 250 is preferably positioned longitudinally along the plunger length so that the front end 238 is not under the breech 224 in the barrel 222, illustrated in FIGS. 17–19. This is to facilitate loading of the collapsible ampule.

At the end adjacent to handle 214 are stop ridges 256. The stop ridges 256 contact the end of the barrel 222 preventing the plunger 214 from extending too far into the barrel 222. This prevents the collapsible ampule from being pushed through the front. Additionally, the flexible fingers 246 provide some frictional resistance to the sliding of the plunger 214 within the barrel 222. This creates a more steady and consistent dispensing of a material from the collapsible ampule. Sputtering of the dispensed material is significantly reduced due to the more even force required to advance the plunger 214.

Accordingly, during collapsing of the collapsible ampule, it is often found that different forces may be required which result in sputtering of the relatively low viscosity material resulting in uneven dispensing. Additionally, the flexible fingers 246 in combination with the reduced intermediate diameter 250 help to retain the plunger 214 within the barrel 222, preventing the plunger 214 from falling out of the barrel 222. However, the plunger 214 is easily removed for cleaning.

The present invention provides a syringe configuration that is particularly adapted and useful in dispensing material from a collapsible ampule containing a relatively low viscosity material. The use of the present invention makes practical the dispensing of small quantities of a low viscosity material contained in a unit dose format. Very consistent doses may be provided utilizing the present invention.

While the present invention has been described with respect to various embodiments, it should be appreciated that various modifications may be made without departing from the spirit and scope of this invention.

What is claimed is:

1. A syringe and collapsible ampule for dispensing a material comprising:
   a barrel having an open end;
   an ampule chamber formed adjacent the open end and having an ampule chamber longitudinal length, said barrel having a breech spaced from the open end;
   a slot having a slot lateral dimension and extending from the breech to the open end;
   an integral unitary collapsible ampule comprising a body portion made of a flexible plastic material that is capable of easily collapsing and folding over onto itself dispensing the material and a dispensing nozzle portion placed within the syringe, the body portion having a body portion longitudinal length and the nozzle portion having a nozzle portion lateral width;
   wherein the ampule chamber longitudinal length is less than the body portion longitudinal length of said integral unitary collapsible ampule and the slot lateral dimension is adapted to permit the nozzle portion of said integral unitary collapsible ampule to pass there through, whereby when said integral unitary collapsible ampule is placed within said ampule chamber in position for dispensing, part of the body portion extends under the breech out of said ampule chamber;
   a plunger sliding within the barrel; and
   wherein said integral unitary collapsible ampule has a hemispherical end and said plunger has a concave front surface,
   whereby the body portion of said integral unitary collapsible ampule may be inserted through the breech and the nozzle portion of said integral unitary collapsible ampule may pass through said slot and lateral movement of the ampule body is prevented during dispensing.

2. A syringe and collapsible ampule for dispensing a material as in claim 1 further comprising:
   a front handle attached to said barrel; and
   a rear handle pivotally attached to said front handle and contacting said plunger.

3. A syringe and collapsible ampule for dispensing a material as in claim 1 further comprising:
   a flexible finger extending radially from an interior surface of said barrel into said bore; and
   an intermediate reduced diameter portion formed in said plunger,
   whereby said flexible finger contacts said intermediate reduced diameter portion of said plunger to hold said plunger within said barrel.

4. A syringe and collapsible ampule for dispensing a material as in claim 1 further comprising:
   a ridge placed on said plunger, whereby said ridge contacts said barrel preventing advancement of said plunger.

5. A syringe and collapsible ampule for dispensing a material comprising:
   a barrel having an open end;
   an ampule chamber formed adjacent the open end and having an ampule chamber longitudinal length, said barrel having a breech spaced from the open end;
   a slot having a slot lateral dimension and extending from the breech to the open end;
   an integral unitary collapsible ampule comprising a body portion made of a flexible plastic material that is capable of easily collapsing and folding over onto itself dispensing the material and a dispensing nozzle portion placed within the syringe, the body portion having a body portion longitudinal length and the nozzle portion having a nozzle portion lateral width;
   wherein the ampule chamber length is between seventy five percent and ninety percent of the body portion longitudinal length of said integral unitary collapsible ampule and the slot lateral dimension is adapted to permit the nozzle portion of said integral unitary collapsible ampule to pass there through; and
   a plunger sliding within the barrel,
   whereby the body portion of said integral unitary collapsible ampule may be inserted through the breech and the nozzle portion of said integral unitary collapsible ampule may pass through said slot.

6. A syringe and collapsible ampule for dispensing a material as in claim 5 further comprising:
   a front handle attached to said barrel; and
   a rear handle pivotally attached to said front handle and contacting said plunger.

7. A syringe and collapsible ampule for dispensing a material as in claim 5 further comprising:
   a flexible finger extending radially from an interior surface of said barrel into said bore;
   an intermediate reduced diameter portion formed in said plunger,
   whereby said flexible finger contacts said intermediate reduced diameter portion of said plunger to hold said plunger within said barrel.

8. A syringe and collapsible ampule for dispensing a material comprising:
   a barrel having an open end and a bore;
   an ampule chamber formed adjacent the open end and having an ampule chamber longitudinal length;
   a breech formed in said barrel and spaced from the open end;
   a slot having a slot lateral dimension and extending from said breech to the open end;
   a collapsible ampule comprising an integral body portion with a convex hemispherical end and a dispensing nozzle portion placed within the syringe, the body portion having a body portion longitudinal length and the nozzle portion having a nozzle portion lateral width;
   wherein the ampule chamber longitudinal length is between seventy-five percent and ninety percent of the body portion longitudinal length of said collapsible ampule and the slot lateral dimension is adapted to permit the nozzle portion of said collapsible ampule to pass there though;
   a plurality of opposing flexible fingers extending radially from an interior surface of said barrel into the bore
   a plunger sliding within said barrel;
   a plunger front having a concave end adapted to receive the convex hemispherical end of the body portion of said collapsible ampule; and
   an intermediate reduced diameter portion formed in said plunger, said intermediate reduced diameter portion longitudinally positioned on said plunger so that when contacting said plurality of opposing flexible fingers said plunger front is not positioned under said breech, whereby the body portion of the collapsible ampule may be inserted through said breech and the nozzle portion of said collapsible ampule may pass through said slot.

9. A syringe and collapsible ampule for dispensing a material comprising:

a barrel having an open end;

an ampule chamber formed adjacent the open end and having an ampule chamber longitudinal length, said barrel having a breech spaced from the open end;

a slot having a slot lateral dimension and extending from the breech to the open end;

an integral unitary collapsible ampule comprising a body portion made of a flexible plastic material that is capable of easily collapsing and folding over onto itself dispensing the material and a dispensing nozzle portion placed within the syringe, the body portion having a body portion longitudinal length and the nozzle portion having a nozzle portion lateral width;

wherein the ampule chamber longitudinal length is at least fifty percent of the body portion longitudinal length of said integral unitary collapsible ampule and the slot lateral dimension is adapted to permit the nozzle portion of said integral unitary collapsible ampule to pass there through;

a plunger sliding within the barrel; and wherein said integral unitary collapsible ampule has a hemispherical end and said plunger has a concave front surface, whereby the body portion of said integral unitary collapsible ampule may be inserted through the breech and the nozzle portion of said integral unitary collapsible ampule may pass through said slot and lateral movement of the ampule body is prevented during dispensing.

10. A syringe and collapsible ampule for dispensing a material comprising:

a barrel having an open end and a breech spaced from the open end;

an ampule chamber formed adjacent the open end and having an ampule chamber longitudinal length;

a slot having a slot lateral dimension and extending from the breech to the open end;

an integral unitary collapsible ampule, placed within said ampule chamber, comprising a body portion made of a flexible plastic material that is capable of easily collapsing and folding over onto itself dispensing the material and a dispensing nozzle portion placed on a front end and a hemispherical shape on a rear end, the body portion having a body portion longitudinal length and the nozzle portion having a nozzle portion lateral width;

wherein the ampule chamber longitudinal length is at least seventy-five percent of the body portion longitudinal length of said integral unitary collapsible ampule and the slot lateral dimension is adapted to permit the nozzle portion of said integral unitary collapsible ampule to pass there through and the open end of said barrel prevents the body portion of said integral unitary collapsible ampule from passing therethrough; and a plunger sliding within the barrel, said plunger having a concave front surface adapted to mate with the hemispherical shape on the rear end of said integral unitary collapsible ampule, whereby the body portion of said integral unitary collapsible ampule may be inserted through the breech and the nozzle portion of said integral unitary collapsible ampule may pass through said slot and the plunger forces the hemispherical shape on the rear end of said integral unitary collapsible ampule towards the dispensing nozzle causing the body portion to fold over onto itself dispensing the material.

* * * * *